United States Patent [19]

Keutenedjian

[11] Patent Number: 4,806,768

[45] Date of Patent: Feb. 21, 1989

[54] INFRA-RED AND ULTRA-VIOLET AIR PURIFYING APPARATUS

[76] Inventor: Ubirajara Keutenedjian, Rua Austria, 95, Sao Paulo, Brazil

[21] Appl. No.: 106,188

[22] Filed: Oct. 8, 1987

Related U.S. Application Data

[63] Continuation-in-part of Ser. No. 917,411, Oct. 10, 1986, abandoned.

[30] Foreign Application Priority Data

Oct. 14, 1985 [BR] Brazil ............................... PI 8505258
Oct. 29, 1985 [BR] Brazil ............................... PI 8505540

[51] Int. Cl.$^4$ ............................................... A61L 9/00
[52] U.S. Cl. ........................................ 250/436; 422/24
[58] Field of Search .................... 98/1; 250/341, 436, 250/438, 455.1; 422/22, 24, 121, 186; 55/279

[56] References Cited

U.S. PATENT DOCUMENTS

| | | | |
|---|---|---|---|
| 1,969,655 | 8/1934 | Mailey | 422/24 X |
| 2,389,698 | 11/1945 | Stowell | 422/121 |
| 2,732,501 | 1/1956 | Blaeker | 422/24 X |
| 3,235,325 | 2/1966 | Storcheim | 422/121 |
| 3,486,308 | 11/1969 | Burt | 422/121 |
| 3,779,710 | 12/1973 | Burstein et al. | 422/121 |
| 4,267,455 | 5/1981 | Keller | 422/24 X |
| 4,468,372 | 8/1984 | Seifert | 422/121 |
| 4,553,992 | 11/1985 | Boissinot et al. | 422/121 |
| 4,621,195 | 11/1986 | Larsson | 250/455.1 |

FOREIGN PATENT DOCUMENTS

| | | | |
|---|---|---|---|
| 729022 | 7/1932 | France | 422/24 |
| 1295774 | 5/1962 | France | 422/24 |
| 2307575 | 11/1976 | France | 422/24 |

Primary Examiner—Harold Joyce

[57] ABSTRACT

Apparatus for the degradation and/or modification of allergenic germs, bacteria, viruses, spores and other substances existing in the air in order to combat some allergies comprises a vertical casing formed by an insulating material suitable to prevent infra-red and ultraviolet rays and heat from propagating. Infra-red lamps are located in the lower part of the casing with an air inlet in the wall of the casing at the level of the infra-red lamps. Ultra-violet lamps are located in the upper part of the casing and an air outlet is provided in the casing wall above the air inlet at an intermediate part of the casing defining an air accumulating chamber inside the casing above the air outlet. The accumulating chamber can be adjusted in size. The air outlet is adjustable downwardly to cause an increase in the accumulating chamber. Also the accumulating chamber can be increased by decreasing the distance between the air outlet and air inlet. Also, the air inlet and air outlet can be provided with adjustable diameters to control the exposure time of the air to be treated by the infra-red and ultra-violet lamps. Two support elements can also be provided to extend over each side of the apparatus to provide a balance-like effect to allow the apparatus to be flexible, thereby to increase or decrease the chamber area.

3 Claims, 2 Drawing Sheets

INFRA-RED AND ULTRA-VIOLET AIR PURIFYING APPARATUS

This is a continuation-in-part application of U.S. Ser. No. 917,411 filed Oct. 10, 1986 now abandoned.

The present invention relates to an apparatus intended to degrade and/or modify microorganisms and other substances existing in the air. The apparatus of the application is efficient to combat some allergies and is particularly a means of bringing benefits to human health. The apparatus has received an original construction so as to be easily operated by the user itself.

As it is known, a number of diseases, mainly respiratory ones, are caused by microorganisms and/or substances suspended in the air. Said microorganisms and substances being breathed by a weak immunological system may attack the organism, causing different pathological reactions and weakening the physical structure of a person.

Modern medical science provides for a number of resources to combat said prejudicial factors, such as: suitable medicaments, inhalation apparatus and the like. However, these can only be used upon medical orientation and prescription.

Known apparatuses for purifying air are disclosed in U.S. Pat. Nos. 2,389,698 to Stowell and 4,621,195 to Larsson. U.S. Pat. No. 2,389,698 relates to the conditioning of air and is particularly directed to a method and apparatus for reducing the harmful effect of pollen and other organic particles in the air. A high coefficient of reflection from two infra-red lamps (250 watts each) is applied, thereby producing an intensive radiation and heat, causing the organic proteinous particles to be denatured. Therefore, pollen and other substances which enter into the apparatus together with air, receive the same intensive and uniform radiation treatment with air sterilization.

U.S. Pat. No. 4,621,195 discloses an apparatus for destroying microorganisms by irradiation with ultra-violet light from a UV-lamp in a major irradiation chamber. The major chamber is divided into minor chambers by means of partition walls. The walls are provided with through-flow openings at their alternate ends, whereby the bacteria-carrying medium is connected reciprocatingly along the UV-lamp and thereby subjected to intensive radiation therefrom over a relatively long period of time.

Nevertheless, said known apparatuses show some inconveniences and operational drawbacks due to the long exposure time required to achieve total purification of the air, intensive radiation and the uniform radiation treatment which prevents the apparatuses from advantageously obtaining microorganisms treated under different degrees.

In order to overcome these inconveniences and restrictions, the present apparatus has been developed to provide for differentiated degrading action over the microorganisms and other substances existing in the air.

An object of the present invention is to provide for an apparatus which actuates over the environment by degrading and/or modifying microorganisms and other substances existing in the air. Such a degradation and/or modification causes the destruction and substantial attenuation of a part of the factors which cause allergies and diseases. The human organism is thereby strengthened to resist the harmful effect of aggressive agents existing in the air.

Another object of the present invention is achieved by the continuous use of the apparatus, thereby strengthening the organism defenses because the apparatus operates as a true vaccinator or air purifier which can be used at home. This objective is achieved due to the differentiated radiation over the substances and microorganisms which enter into the apparatus and which are differentialy degraded or treated when leaving the apparatus.

In order to achieve the above-mentioned objectives, the apparatus of the present invention uses infra-red and ultra-violet radiations together. Heat derived from the infra-red radiation causes the micro-organisms to become more susceptible to die and weaken in view of the thermal shock. Therefore, the degrading effect is most efficient and obtained in a shorter period of time by using both ultra-violet and infra-red radiations. Degrading is faster and does not need high temperatures.

The apparatus of the present invention may be conveniently dimensioned to be used everywhere e.g.: at home, office, industrial plants, hospitals and elsewhere.

The present invention may be more fully understood on basis of the following description in view of the drawings attached hereto in which.

Figure 1A:
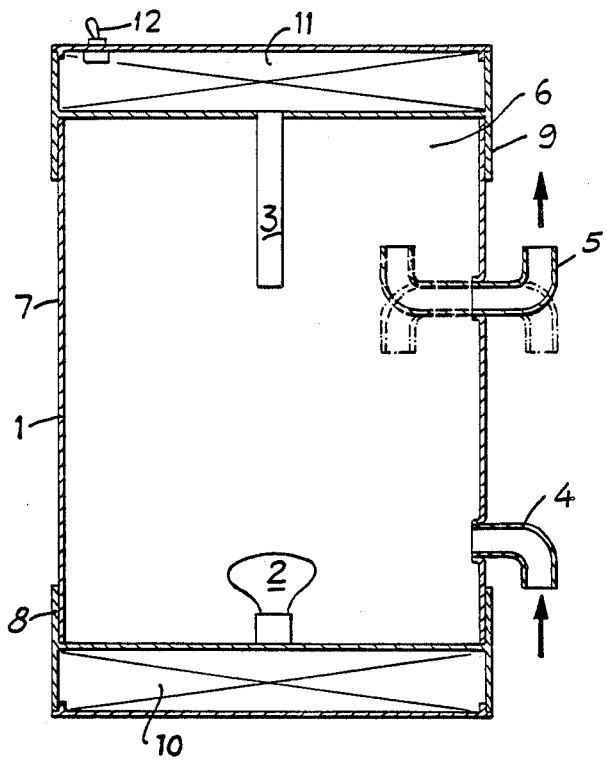
FIG. 1A is a section view of a first embodiment of the apparatus of the present invention.
Figure 1B:
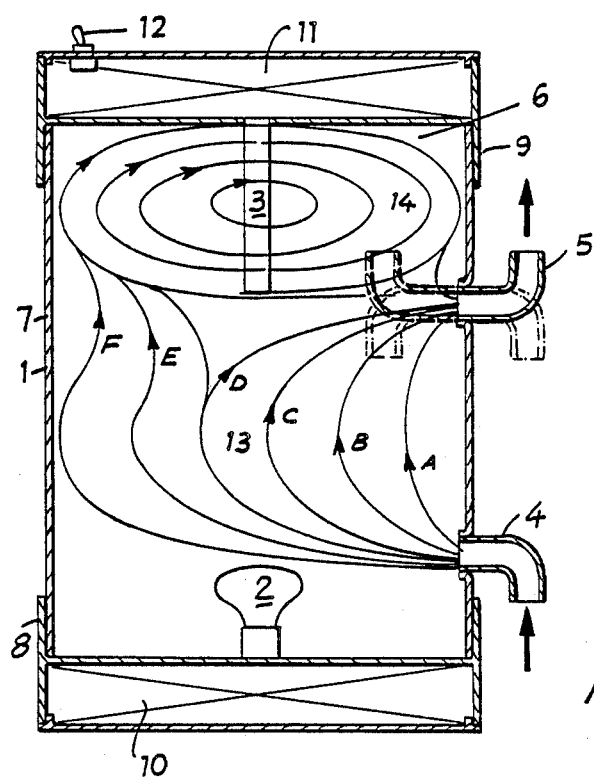
FIG. 1B is a section view of the apparatus of FIG. 1 of the present invention, showing the different air currents entering and leaving the chamber.
Figures 2A, 2B:
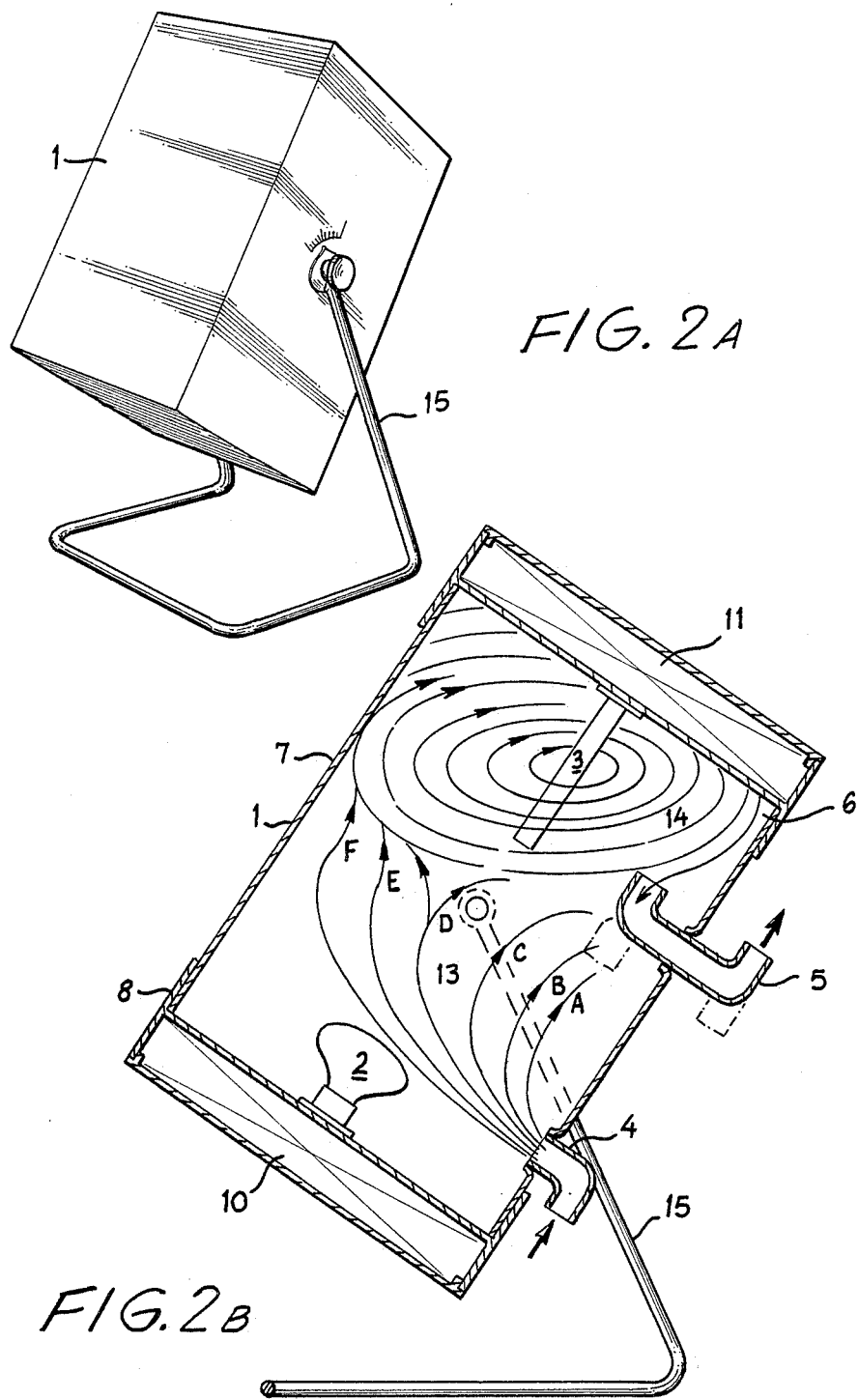
FIG. 2A is a persepective view of a second embodiment of the apparatus of the present invention.
FIG. 2B is a lateral sectional view of the second embodiment of the apparatus of the present invention.

The apparatus according to the present invention shown in FIGS. 1A and 1B includes a casing 1 housing lower infra-red lamp 2 and upper ultra-violet lamp 3, having a lower lateral inlet 4 for the air to be treated which is forced by convection to circulate inside said casing 1, during which time microorganisms and substances are subjected to the action of ultra-violet and infra-red rays emitted by the lamps 2 and 3. The air leaves the casing 1 by means of an upper lateral outlet 5 which may be placed at an intermediate or variable level of the casing so as to define inside thereof an upper accumulating chamber 6 in which the air is retained for a longer period of time in view of the heat created by the radiations. Optionally, the apparatus may be provided with means to promote forced circulation of the air inside the apparatus, so as to adjust the period of contact between the air to be treated and infra-red and ultra-violet radiations, gradual degrading time of the microorganisms being respected.

According to the drawings, the apparatus of the present invention comprises a vertical casing 1, formed by a material which prevents infra-red and ultra-violet radiation from being outwardly propagated. Said casing 1 houses lower infra-red and upper ultra-violet lamps 2 and 3, an inlet opening 4 being provided in the housing wall at the level of the infra-red lamp, through which air to be treated is introduced by convection. A treated air outlet 5 is provided above said inlet 4. Said air outlet 5 may be placed at an intermediate level of the casing wall so as to define inside this latter and above said outlet 5, an air accumulating chamber 6 or 14 in which the air is kept for a longer period of time under the action of the lamps, part of this air being mixed by venturi to the flow of treated air which is not accumulated and thus controlling the conditions of the air leaving the apparatus. FIG. 1B shows air flows 13A, B, c, D and F in the accumulating chamber 14 with different paths and exposure time.

In the first embodiment of the apparatus, casing 1 is formed by an intermediate body 7 of any section, receiving respective lower 8 and upper 9 covers at its ends, said covers supporting said infra-red 2 and ultra-violet 3 lamps respectively, as well as defining chambers 10 and 11 which house the electrical elements which enable operation of the lamps. Optionally, an on/off switch 12 may also be incorporated in casing 1 to turn on and off the apparatus.

In order to control the exposure time of the air to be treated under infra-red and ultra-violet rays, besides the accumulating chamber 6, inlet 4 and outlet 5 may be provided with different diameters, in different apparatuses in order to determine different flows or else making an adjustable outlet and inlet.

Another way of controlling the exposure time of the air to the radiations from the lamps, comprises providing for the lamps with different power ratings which besides acting on the air with different intensities causes faster or slower circulation thereof from the inlet to the outlet, thus regulating desired levels of action of the apparatus over the air to achieve degradation, in scale.

Another means of causing interference to the air circulation speed inside the apparatus and consequently on the exposure time thereof to the infra-red and ultra-violet radiations emitted by the lamps, comprises to provide the apparatus with internal adjustable electrical resistances which are capable of regulating the interior heat at levels corresponding to the desired circulation speed, as well as helping in the germ degradation and/or modification.

Inlet 4 and outlet 5 are preferably formed by U or L shaped tubes and/or shields provided in front thereof and inside the apparatus, their main purpose being to prevent light, ultra-violet and infra-red rays from escaping. Said inlet 4 and outlet 5 are rotatably mounted in the casing wall and are capable of being adjusted downwardly or upwardly, thereby increasing or decreasing the radiation.

In opposition to the known apparatuses which treat uniformly the air which enters thereinto, the apparatus of the present invention discloses exposure of the air to different radiation times in view of the construction of the apparatus.

The structure of the present invention includes a chamber 6 having a lower outlet level 5, heat accumulated in said chamber 6 flowing to the level of outlet 5, and air heated by infra-red 2 is raised by convection and is received into chamber 6. The same amount of air leaves through outlet 5 drawing a number of heat streams containing microorganisms and substances (13 A,B,C, and D).

The apparatus showing these features is used preferably in the user's bedroom during his sleeping hours at a distance of one or more meters, as a means to prevent allergic processes, that is, before the illness settles deeply into the body, and of course it can also be employed in the treatment of pathological states already set-in or by any other way or in other locations provided the user is exposed for long periods to the air coming from the apparatus.

Thus when the apparatus is connected, its inside will heat-up and by mere convection and/or with the help of fans, the room air is drawn into its housing and exposed, during a time period to be regulated by the regulating means above described, to the infra-red and ultra-violet radiations from the lamps and later returned to the room adequately treated, that is, the germs and substances have already been destroyed and/or modified.

As the user of the apparatus breathes this air his defenses and consequently his resistance to aggressive agents that cause allergies and other diseases affecting mainly the respiratory tract will be increased.

This results from the unequal action due to the different radiation treatment time.

As can be seen in FIG. 2B, in which the elements similar to those in the first embodiment have the same reference numerals according to the present invention as an alternative embodiment to increase or decrease the chamber area, the apparatus may be provided with two support elements extending over each side of the apparatus. Said two support elements 15 are useful to enable the apparatus to have a balance-like effect allowing the apparatus to be flexible, thereby increasing or decreasing the chamber area.

On the other hand, as it is known in the art, photons emitted from ultraviolet rays release electrons. These electrons actuate against metals thereby causing ionization of the air.

Said known feature is used in the present invention with a great efficiency because both ultraviolet and infra-red rays actuate together against the inner walls of the chamber thereby causing a most intensive ionization of the air passing through the accumulating chamber 6.

I claim:

1. Apparatus for the degradation and modification of germs, bacteria, viruses and other substances existing in the air, comprising a vertical casing (1) infra-red lamps (2) located in the lower part of said casing, ultra-violet lamps (3) located in the upper part of said casing an air inlet (4) provided in a wall of the casing substantially at the level of the infra-red lamps, an air outlet (5) provided in the casing wall above said air inlet, said air inlet and air outlet being positioned at one side of said casing, and bottom and top covers (10,11) respectively closing bottom and top portions of said casing said air outlet being located at an intermediate part of said casing so that a heated air accumulating chamber (6) is defined inside the upper portion of said casing above said air outlet.

2. Apparatus according to claim 1, wherein said infra-red and ultra-violet lamps (2,3) act on the air which enters into said casing 91) through said inlet (4) under a convection effect which causes different air currents (13A,B and C; 13D; and 13E and F) to be created, a first group (13A,B and C) of said air currents reaching said air outlet (5) before the remainder of said air currents and being subjected to a relatively short period of exposure to said lamps, a part of another air current (13D) being directed towards said accumulating chamber (6) and another part of said other air current (13D) being directed towards said air outlet so as to be subjected to a longer period of exposure to said lamps than said first group of air currents, and a third group (13E and F) of said air currents being circulated inside said air accumulating chamber and being subjected to the longest period of exposure to said lamps and drawing out said first group (13A, B and C) of air currents by Venturi through said air outlet.

3. Apparatus according to claim 2, wherein said outlet (5) is U-shaped and is rotatably mounted in the casing wall and includes nozzles located internally and externally of said casing (1), and said air outlet being rotatable around an axis thereof to adjust the position of said nozzles downwardly and upwardly, whereby in a downward position of said nozzles they facilitate escape of said first group (13A, B and C) of said air currents and said other part of said other air current (13D) and simultaneously increase the volume of said accumulating chamber (6), and in an upward position of said nozzles the path of said first group (13A,B and C) of said air currents is increased causing the period of exposure to said lamps to be increased, thereby to obtain a variation of the exposure period to said lamps of said first group of air currents to achieve a different degrading effect.

* * * * *